United States Patent
Weiss

[19]

[11] Patent Number: 6,096,046
[45] Date of Patent: Aug. 1, 2000

[54] SURGICAL INSTRUMENT

[76] Inventor: Sol Weiss, 17144 Bullock St., Encino, Calif. 91316

[21] Appl. No.: 09/104,303

[22] Filed: Jun. 24, 1998

[51] Int. Cl.[7] ............................ A61B 17/42; A61B 17/46
[52] U.S. Cl. ............................................. 606/119; 600/210
[58] Field of Search ............................ 606/119; 600/184, 600/185, 208, 214, 215, 201, 211

[56] References Cited

U.S. PATENT DOCUMENTS

| | | | |
|---|---|---|---|
| 4,337,763 | 7/1982 | Petrassevich | 600/220 |
| 4,385,626 | 5/1983 | Danz | 600/210 |

Primary Examiner—Michael Buiz
Assistant Examiner—Vy Q. Bui
Attorney, Agent, or Firm—Gerald L. Price

[57] ABSTRACT

A surgical instrument for spreading apart the internal organs of a patient. The instrument includes a scissors-like main body portion having a plurality of blades that open to spread apart the area being examined so that a surgical tool can be inserted therein. The instrument can be withdrawn or moved out of the area of view by allowing the surgical tool to pass through a gate formed between the spread-apart blades while maintaining the spread-apart condition of the area being examined. The blades can then be restored to their closed position after the tool is withdrawn.

11 Claims, 6 Drawing Sheets

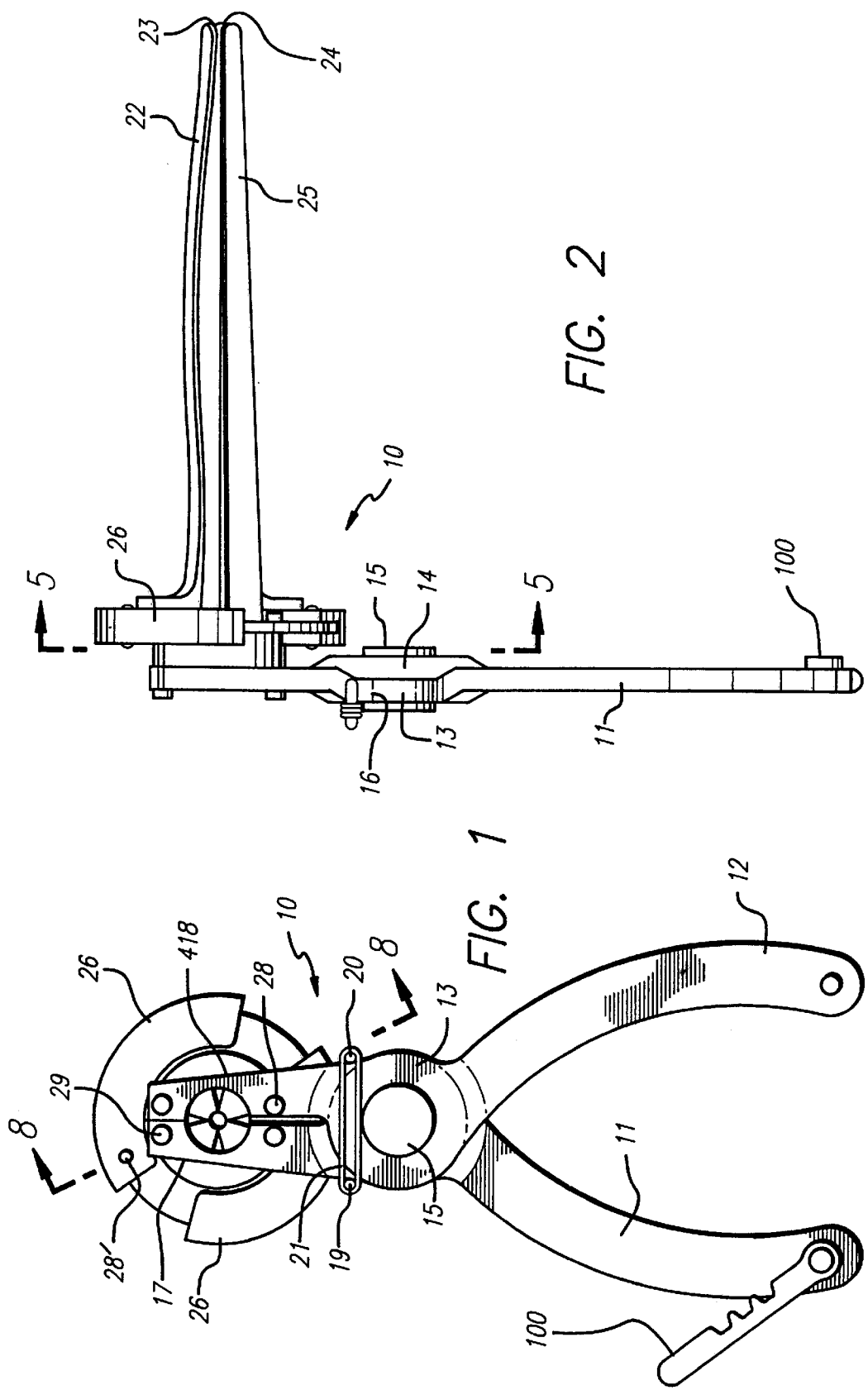

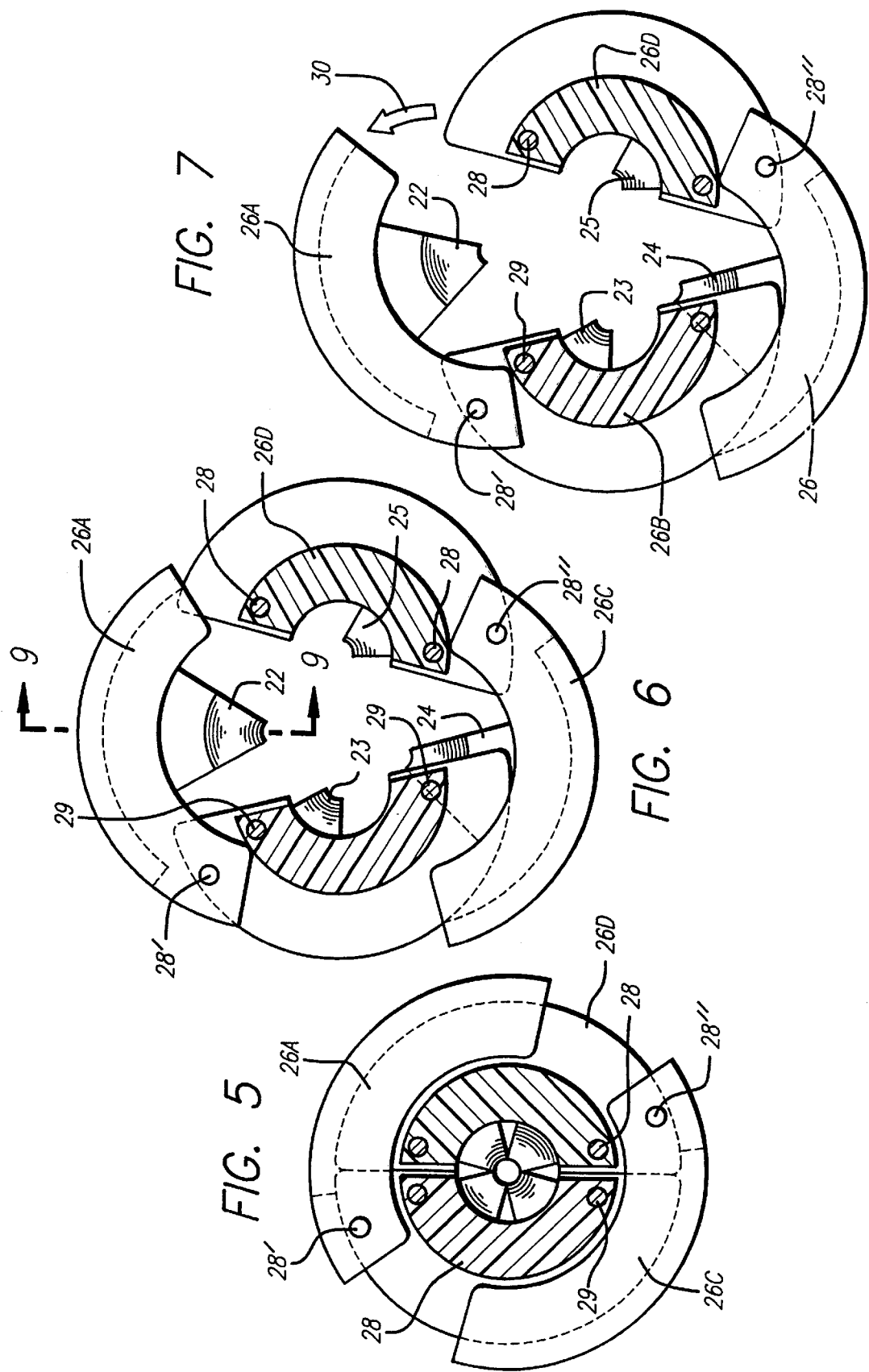

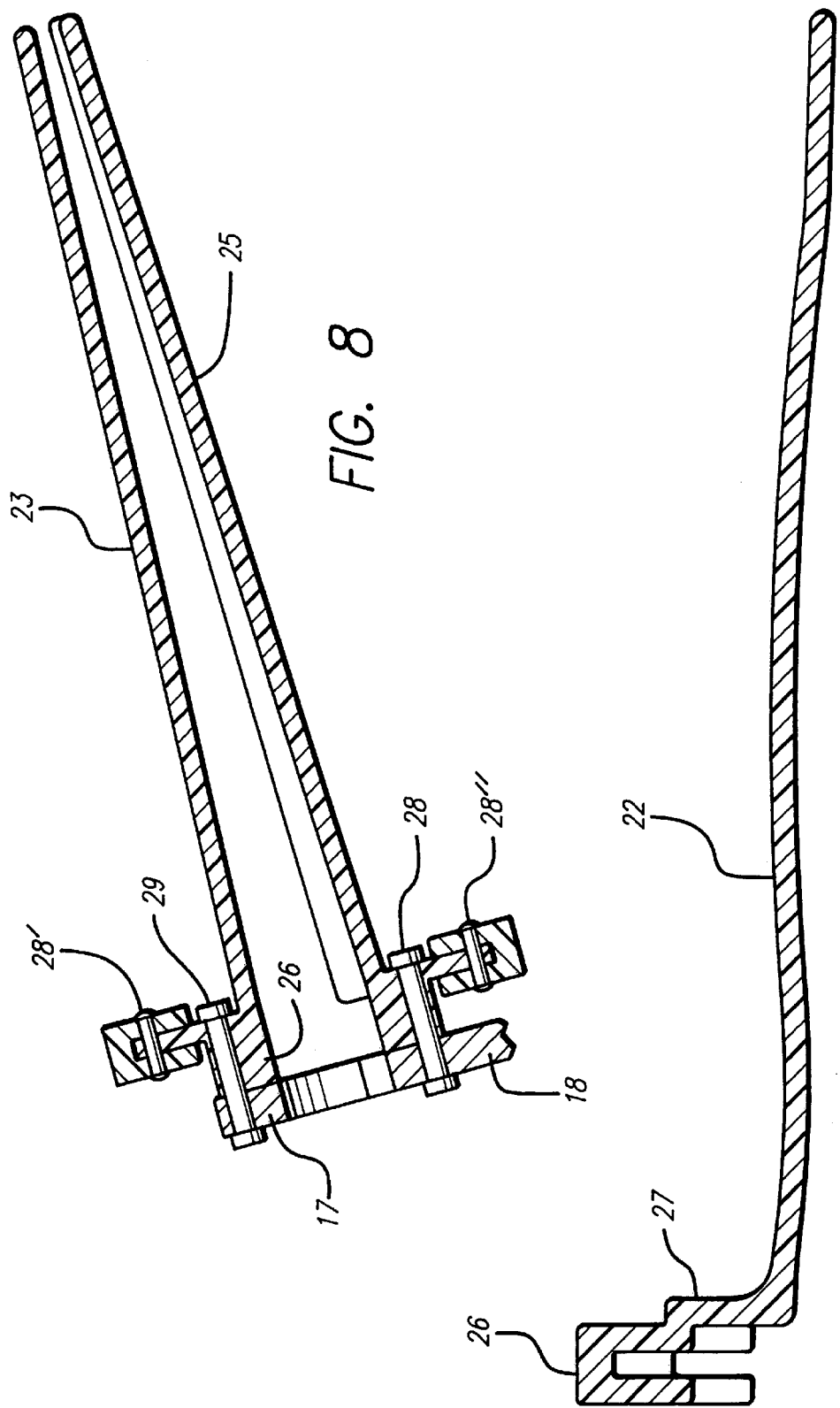

SURGICAL INSTRUMENT

BACKGROUND OF THE INVENTION

1. Field of the Invention

The invention relates to surgical instruments; and, more particularly, to diagnostic and surgical instruments for use in abdominal, thoracic or vaginal and anal surgical procedures that may also include endoscopies.

2. Related Art

Certain surgical and diagnostic devices are known for examining vaginal and other cavities. For example, women of a certain age should have a diagnostic pap smear annually. Certain prior art devices, known as speculums, are used which consist of a pair of wide or broad blades, but such are uncomfortable to the patient, causing much discomfort.

Also, when such instruments are used in examining a body cavity, such as the vagina, a second instrument is inserted into the vagina through the speculum. Such an instrument is called a lateral vaginal retractor and is used to retract the vaginal side walls which normally obstruct the doctor's view into the patient's cervix. During a surgical procedure, the surgeon needs to insert a clamp, a source of lighting, a suctioning catheter, and irrigation tube through the speculum, thus further obstructing the surgeon's view of the cervix which might interfere with the surgical procedure being performed.

There is a need for a surgical and diagnostic instrument which eliminates the need for a lateral vaginal retractor during vaginal surgery. Such an instrument should be anatomically designed with a narrow oval shape in its closed position to allow it to be inserted comfortably into the patient's vagina without the discomfort generally associated with a conventional speculum.

SUMMARY OF THE INVENTION

It is an object of this invention to provide a surgical and diagnostic instrument for examining a patient's body cavity, such as a vagina, eliminating the need for a lateral vagina retractor during surgery.

It is another object of this invention to carry out the foregoing object that is anatomically designed (four quadrant retraction allows the blades to be less width producing a narrower instrumentation) to cause little if any discomfort to the patient.

It is still another object of this invention to provide a multi-bladed vaginal diagnostic and surgical instrument which is quickly and easily activated to expand the blades with slight rotation movement and little discomfort to the patient.

It is further an object of this invention to carry out the foregoing objects allowing easy insertion into the body cavity being examined without allowing the instrument to slip out of the body cavity during examination.

These and other objects are preferably accomplished by providing a surgical instrument for spreading apart openings of natural orifices or surgically made openings to perform procedures on internal structures and/or organs of a patient. The instrument includes a scissors-like main body portion having a plurality of blades that open to spread apart the area being examined so that a surgical tool can be inserted therein. The instrument can be withdrawn or moved out of the area of view by allowing the surgical tool to pass through a gate formed between the spread-apart blades while maintaining the spread-apart condition of the area being examined. The blades can then be restored to their closed position after the tool is withdrawn.

BRIEF DESCRIPTION OF THE DRAWING

FIG. 1 is a front elevational view of a surgical instrument in accordance with the teachings of the invention;

FIG. 2 is a side elevational view of the surgical instrument of FIG. 1;

FIG. 5 is a view taken along lines 5—5 of FIG. 2;

FIGS. 6 and 7 are views taken along lines 6—6 and 7—7, respectively, of FIG. 4 illustrating the movement of the blades from the FIG. 4 position to the fully open position shown in FIG. 7;

FIG. 8 is a view taken along lines 8—8 of FIG. 1;

FIG. 9 is a view taken along lines 9—9 of FIG. 6; and

DESCRIPTION OF THE PREFERRED EMBODIMENT

Figure 4:
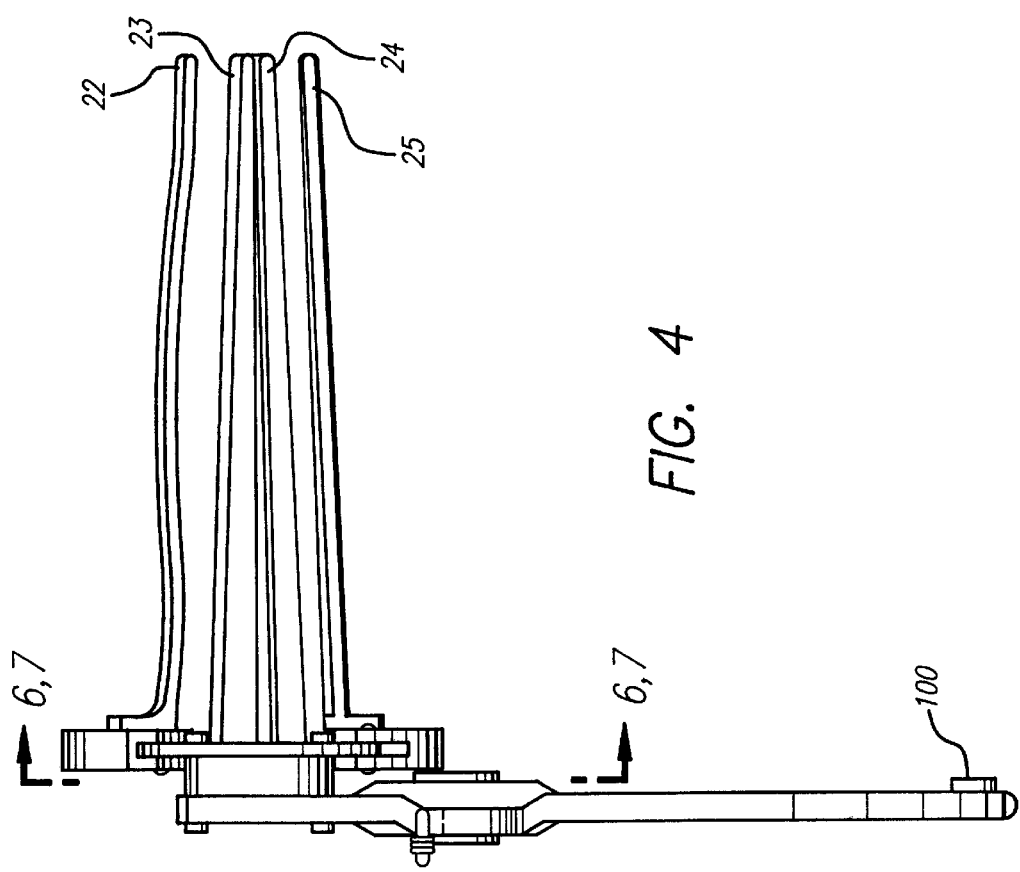
FIG. 4 is a view similar to FIG. 2 illustrating the position of the blades when the instrument is in the FIG. 3 condition.

Referring now to FIG. 1 of the invention, a surgical instrument 10 is shown in closed position. Instrument 10 has a pair of arcuate handles 11, 12 each integral and extending from a boss 14, 13, respectively (see also FIG. 2). Bosses 13, 14 have aligned apertures receiving a pin 15 therethrough. As in FIG. 2, pin 15 may be enlarged at each end providing a diameter greater than the aligned apertures (see dotted lines 16 in FIG. 2) so that bosses 13, 14 are retained on pin 15.

Figure 3:
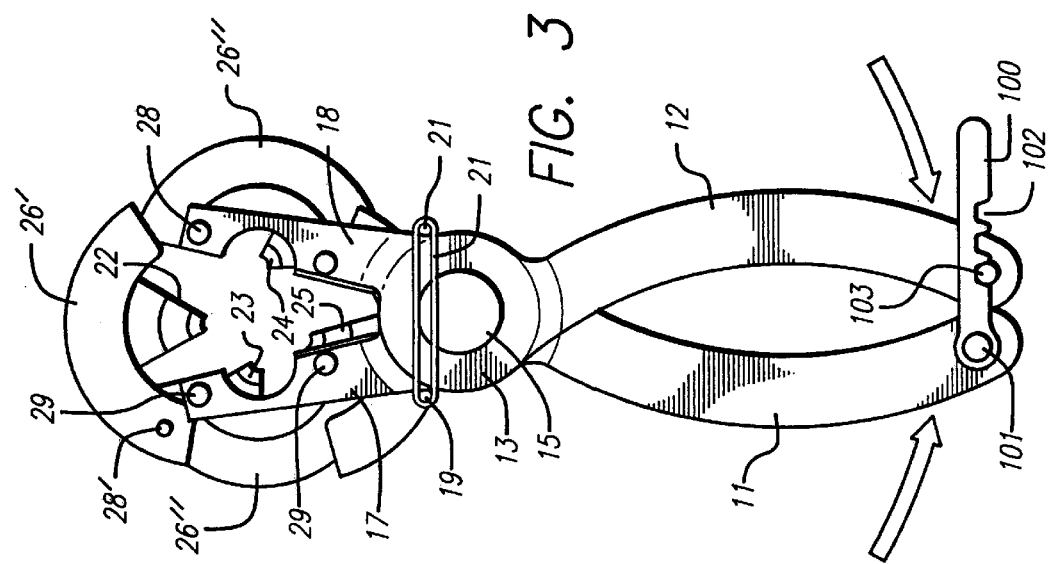
FIG. 3 is a view similar to FIG. 1 showing the blades of the instrument in a partly open condition.

As seen in FIG. 3, boss 14 has an extension arm 17 integral therewith. Boss 13 has an extension arm 18 integral therewith. Thus, arm 11, boss 14, and arm 17 may be one integral piece pivotable on pin 15.

A first pin 19 is mounted to arm 17 adjacent boss 14 and a second pin 20 is mounted to arm 18 adjacent boss 13. A rubber band 21 encircles spaced pins 19, 20 thus biasing arms 17, 18 together to the closed or FIG. 1 position.

Four blades 22 to 25 are provided, each blade having a blade base, (see particularly FIG. 9—although blade 22 differs slightly from blades 23 to 25, as will be discussed, the bases are identical). The blades may be arcuate in cross-section. Thus, the bottom of each blade curves into a blade bottom portion 27 integral with or otherwise secured to its respective base, such as 26. Blade 22, and only blade 22, may be curved as seen in FIG. 9 for relieving pressure on the pubic bone or bladder of the patient. Blade 23 (FIG. 6) is secured to base 26 which is in turn secured to arm 17 (FIG. 3) by fastening pins 29. Blade 24 is secured to base 26C. Blade 25 is secured to base 26D which is in turn secured to arm 18 (FIG. 3) by fastening pins 28. The base 26 of blade 22 is pivotally connected to the base 26B of blade 23 by a pivot pin 28'. The base 26D of blade 25 is pivotally connected to the base 26C as blade 24 by a pivot pin 28".

Looking at FIGS. 1 and 2, the blades are in the closed position. When handles 11, 12 are squeezed together against the bias of band 21, as indicated by the arrows in FIG. 3, the arms 17, 18 move away from each other as seen in FIG. 3, thus separating the blade (see FIG. 4). This can also be seen in FIG. 5 wherein the bases 26A to 26D, at the initial position shown in FIG. 1, move apart to the FIG. 6 position carrying blades 22 to 25 secured thereto at their base bottom portions 27 with them. Thus, the bases of two blades, as blades 23, 24, are secured to arms 17, 18, respectively, whereas the bases of blades 22, 25, are pivotally connected to adjacent bases (see FIGS. 3 and 5) by pivot pins 29 to the fully open position shown in FIG. 7 forming a gap or opening leading into the interior thereof as indicated by arrow 30. Release of handles 11, 12 returns the blades to the FIGS. 1 and 2 position.

If desired, a locking lever 100 (FIG. 3) may be provided pivotally connected to handle 11 by a pivot pin 101. Lever 100 has a plurality of spaced notches 102 adapted to engage pin 103 on handle 12 to lock the handles together in differing positions.

Figure 10:
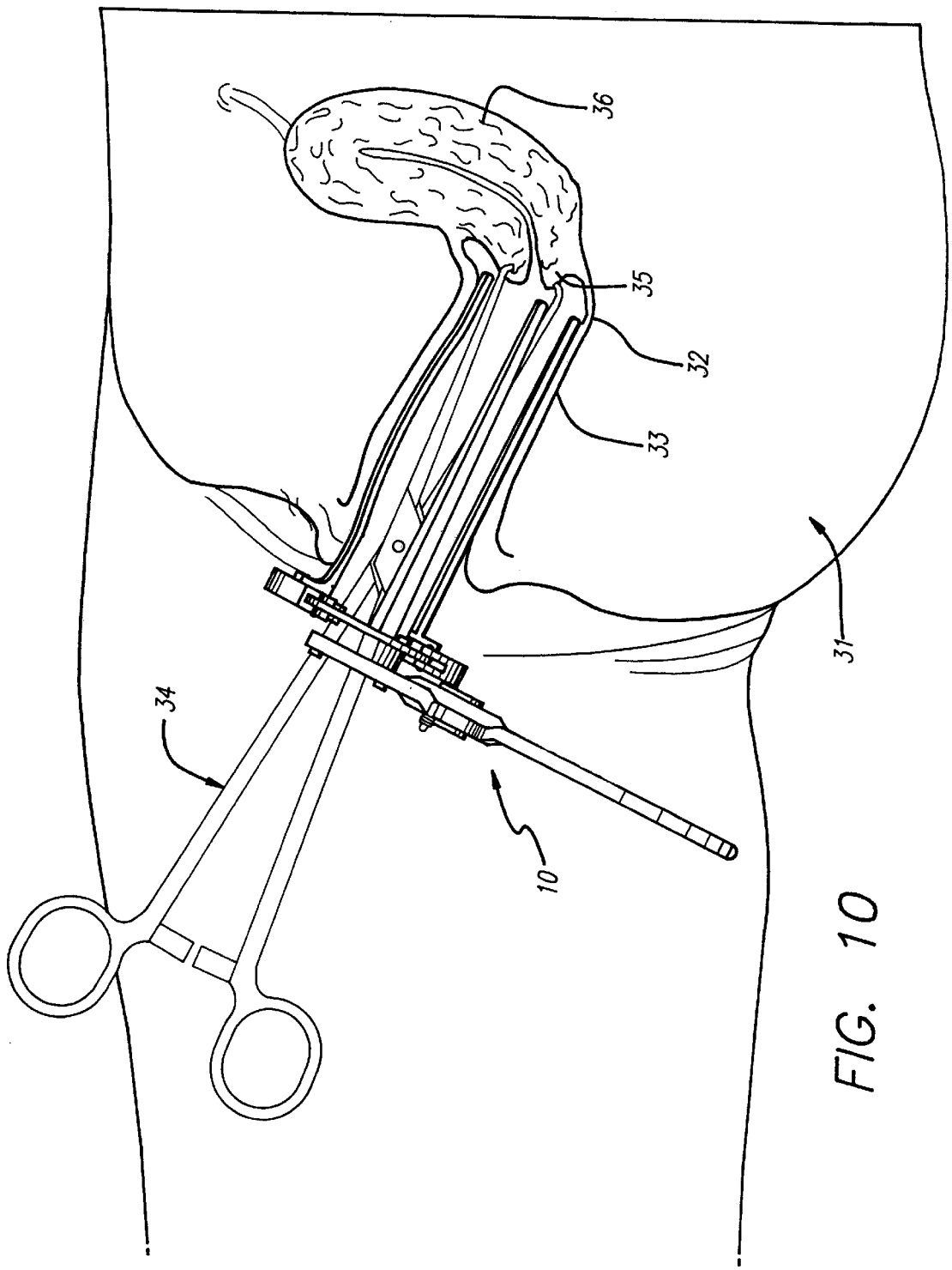
FIG. 10 is a perspective view illustrating the operation of the instrument of FIGS. 1 to 9 in conjunction with a conventional tenaculum for examining the abdomen of a patient.
Figure 11:
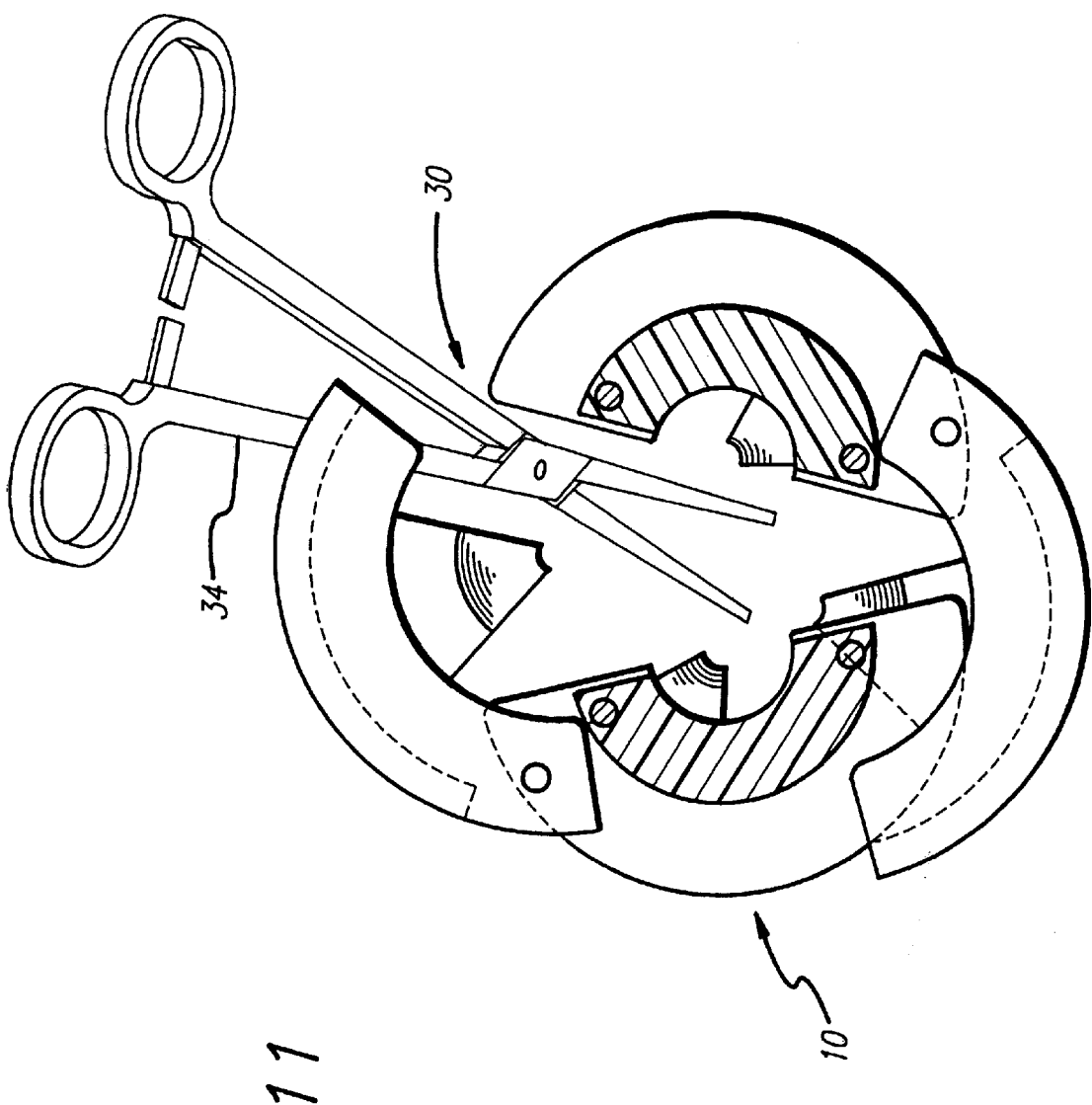
FIG. 11 is a perspective view illustrating the operation of the instrument of FIGS. 1 to 9 showing a conventional tenaculum extending through the gate of the instrument so as not to interfere with the surgeon's vision during surgery.

The operation of instrument 10 will now be discussed. The abdomen 31 of a patient is shown in FIG. 10, Surgical instrument 10, which in the FIG. 4 position has a narrow oval configuration in cross-section, is shown as having been inserted into the vagina 32 and opened to spread apart the blades 22 to 25 as in FIG. 4 holding wide open the vaginal pouch 33. A conventional tenaculum 34 is now inserted between the open blades of instrument 10 grasping the cervix 35 of the uterus 36. The surgeon or doctor can then carry out his or her diagnostic and therapeutic procedures on the patient's pelvic organs. The instrument 10 can be moved off to the side allowing the tenaculum 34 to pass or go through the gate 30 (FIG. 11) as the instrument 10 is moved and tilted out of vision of the doctor. Gate 30 may be about ½" to 1" wide. This provides better visibility for diagnostic procedures and insertion of further instruments, if necessary.

Gate 30 allows the tenaculum 34 to be bypassed by the instrument 10. That is, the open gate 30 is not a barrier to the tenaculum 34 as the instrument 10 is moved off to the side and the tenaculum 34 passes through the gate 30.

There is thus disclosed a surgical instrument which is a four-way spreader useful in examining the body of a patient. The spreader holds open the area one desires to examine, such as the vaginal pouch leading to the uterus, and can be moved quickly and easily off to the side upon insertion of a conventional diagnostic tool, such as a tenaculum, to provide better visibility and maneuverability. The instrument can be made of any suitable materials, such as plastic.

It can be seen that there is a disclosed a surgical and diagnostic instrument for examining body cavities of a patient, particularly women's vaginas.

Only one instrument is needed instead of two, thus reducing the cost associated with such a procedure which is of prime importance in this age of managed care. With one instrument and one operation, all four (4) quadrants of the instrument are spread to keep tissues from cascading into the incision site, and a more circular opening can be obtained. The four (4) blades also allow for less slippage from the organ while the instrument is expanded as compared with a conventional two-blade instrument.

Although particular sized blades are disclosed for examining a woman's vagina, the instrument can be used with different size blades for the following applications:
1. Vaginal
2. Rectal
3. Ear, nose and pharyngeal
4. Laparoscopies
5. Abdominal and thoracic surgeries A fiberoptic cord may be attached to the instrument for additional lighting in the body canal. The gate, which swings open at the top of the instrument, allows one to position the irrigation tube and clamp outside of the surgical site, thus eliminating the obstruction encountered by current instruments as heretofore described.

It is further the scope of this invention to have the capability of making disposable, removable blades (different size blades for different procedures) with a stainless steel reusable handpiece. This will assist in preventing contamination between patients and thus will make these procedures safer to the patients in this age of HIV and hepatitis contagious diseases.

In conclusion, the diagnostic and surgical instrument as disclosed herein provides a single operation instrument with a four-way blade spread. All four blade quadrants are spread to keep tissues from cascading into the incision site. A more circular instrument opening is available. A variety of larger instrument openings are possible due to the lockable lever which may have been somewhat limited in prior instruments due to their housing. This is important for closed system surgeries. The instrument's gradual spread with handles allows better control of the instrument depth. Manual control allows for less slippage and a plurality of tubes may not be necessary to increase the size of openings.

The use of four blades allows for less slippage when expanding than two blades. The instrument's smaller housing on top thereof makes the instrument more adaptable to many uses. The curved housing blades allow for better placement of the instrument in surgeries and vaginal exams. The instrument disclosed herein allows the use of different shapes of blades as seen on other retractors for other types of surgical and/or examination procedures. The instrument herein is cheaper and easier to manufacture and assemble and thus reduces cost. It requires less steps than prior art devices for performing the procedure.

The instrument can be made entirely of any suitable materials, such as plastic material. Some of the uses of the instrument herein are:
Skin and subcutaneous tissue:
1. Foreign bodies
2. Lymph nodes
3. Ganglionectomy
4. Laparoscopy and other abdominal surgery
5. Spinal (neurosurgical)
6. Neck surgeries
   a. Emergency (closed system)
   b. Permanent
7. Thoracotomy
   a. Emergency
   b. Elective
8. Facial procedures The instrument can be used for the following examinations:
1. Vaginal
2. Rectal
3. Ear and nasal and, possibly, pharyngeal Fiberoptic blades can be provided for deep lighting.

Although a particular embodiment of the invention is disclosed, variations thereof may occur to an artisan and the scope of the invention should only be limited by the scope of the appended claims.

I claim:

1. A surgical instrument for carrying out diagnostic and therapeutic procedures on an interior organs of a human body comprising:

a pair of handles pivotally connected together;

an arm extending from each handle, each arm having a base pivotally secured thereto;

a blade connected to each base extending away from said base;

a pair of bases, each having a blade connected thereto, each of said blades connected to said pair of bases being pivotally connected to respective ones of said bases pivotally secured to said arms; and said arms being normally biased to a position adjacent one another whereby said blades secured to said arms are adjacent each other and the blades mounted on said bases pivotally connected to said bases secured to said arms are adjacent each other whereby, when said handles connected to said arms are pivoted against the normal bias of said arms, said blades spread apart.

2. The instrument of claim 1 wherein, when said handles are pivoted to a position spreading apart said blades, an open gap is provided between at least two of adjacent bases.

3. The instrument of claim 1 wherein one of said blades is curved in cross-section adjacent its point of connection to its respective base.

4. The instrument of claim 1 wherein said arms are normally biased by an elastic band encircling a pin fixed to each of said arms.

5. The instrument of claim 1 wherein each of said handles is integral with its respective arm and of one piece lying in a generally horizontal plane, said blades extending generally normal therefrom.

6. The instrument of claim 5, wherein said handle and arm is of stainless steel.

7. The instrument of claim 5 wherein said handle and arm is of plastic.

8. The instrument of claim 1 wherein each of said handles is coupled to a boss having its respective arm integral therewith and extending therefrom, said bosses being pivotally interconnected.

9. The instrument of claim 8 wherein said arms are biased by a resilient member encircling a pair of spaced pins, one of said pins being integral with and fixed to one of said arms, and the other of said pins being integral with and fixed to the other of said arms.

10. The instrument of claim 9 including locking latch means associated with the handles to hold the handles in a fixed open position while a surgical procedure can be undertaken.

11. The instrument of claim 10 wherein said fixed open position is variable.

* * * * *